(12) United States Patent
Berube et al.

(10) Patent No.: US 6,471,696 B1
(45) Date of Patent: Oct. 29, 2002

(54) MICROWAVE ABLATION INSTRUMENT WITH A DIRECTIONAL RADIATION PATTERN

(75) Inventors: Dany Berube, Fremont, CA (US); Jules Gauthier, Laval (CA)

(73) Assignee: AFx, Inc., Fremont, CA (US)

( * ) Notice: Subject to any disclaimer, the term of this patent is extended or adjusted under 35 U.S.C. 154(b) by 0 days.

(21) Appl. No.: 09/547,629

(22) Filed: Apr. 12, 2000

(51) Int. Cl.[7] .............................................. A61B 18/18
(52) U.S. Cl. ............................ 606/33; 607/98; 607/101
(58) Field of Search ........................... 606/33, 41, 32, 606/39, 35; 607/101, 102, 159, 156, 96, 98, 99

(56) References Cited

U.S. PATENT DOCUMENTS

| | | | |
|---|---|---|---|
| 4,601,296 A | * | 7/1986 | Yerushalmi .................. 607/101 |
| 4,643,186 A | * | 2/1987 | Rosen et al. ................. 607/156 |
| 4,785,815 A | | 11/1988 | Cohen |
| 4,823,812 A | * | 4/1989 | Eshel et al. .................. 607/101 |
| 5,314,466 A | | 5/1994 | Stern et al. |
| 5,364,392 A | | 11/1994 | Warner et al. |
| 5,370,644 A | | 12/1994 | Langberg |
| 5,454,370 A | | 10/1995 | Avitall |
| 5,603,697 A | | 2/1997 | Grundy et al. |
| 5,788,692 A | | 8/1998 | Campbell et al. |
| 5,800,494 A | | 9/1998 | Campbell et al. |
| 5,836,990 A | | 11/1998 | Li |
| 5,861,021 A | | 1/1999 | Thome et al. |
| 5,954,662 A | | 9/1999 | Swanson et al. |
| 5,957,842 A | | 9/1999 | Littmann et al. |
| 6,233,490 B1 | * | 5/2001 | Kasevich .................... 607/101 |
| 6,245,062 B1 | * | 6/2001 | Berube et al. ................. 606/33 |
| 6,287,302 B1 | * | 9/2001 | Berube ........................ 606/33 |

FOREIGN PATENT DOCUMENTS

WO  00/24463  4/2000

* cited by examiner

Primary Examiner—Linda C. M. Dvorak
Assistant Examiner—David M. Ruddy
(74) Attorney, Agent, or Firm—Beyer Weaver & Thomas, LLP

(57) ABSTRACT

A medical instrument is disclosed. The medical instrument includes a transmission line suitable for the transmission of electromagnetic energy and an antenna coupled to the transmission line. The antenna is configured for generating an electromagnetic field sufficiently strong to cause tissue ablation. The medical instrument further includes a reflector arranged to be electrically coupled to the transmission line. The reflector is positioned laterally to a first side of the antenna and configured for redirecting a portion of the electromagnetic field to a second side of the antenna opposite the reflector, wherein a majority of the electromagnetic field is directed away from the second side of the antenna.

42 Claims, 7 Drawing Sheets

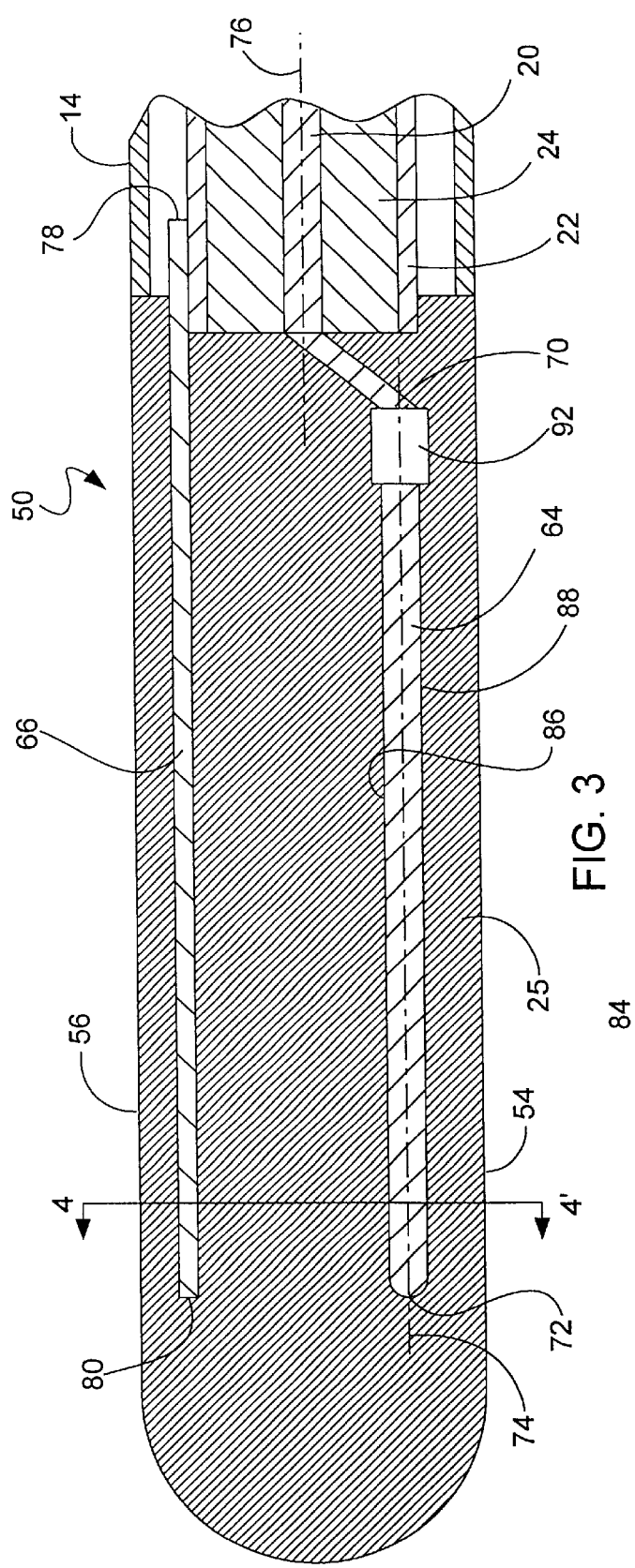
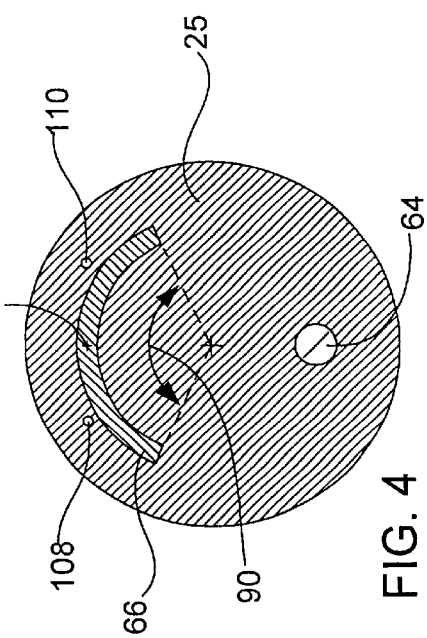
FIG. 3
FIG. 4

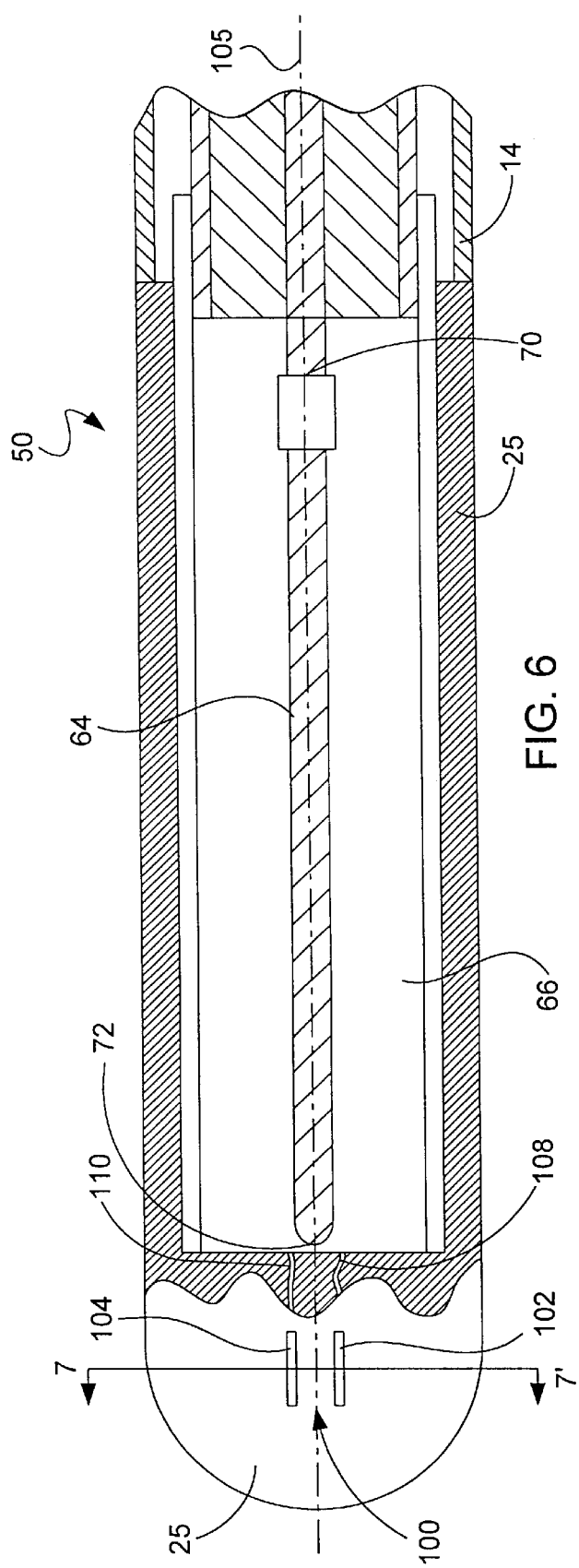
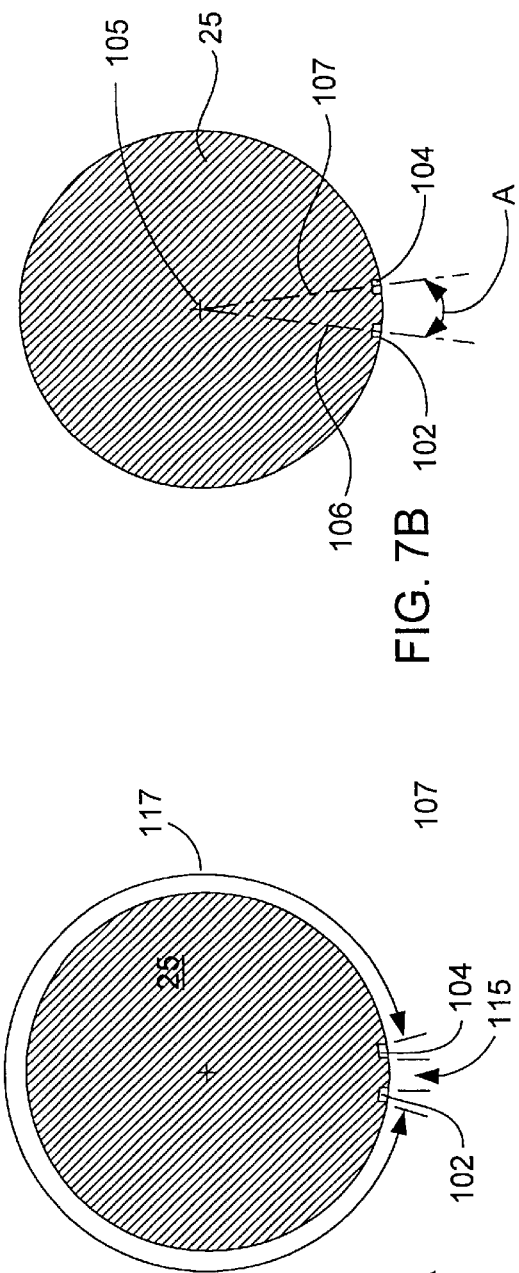
FIG. 6
FIG. 7A
FIG. 7B

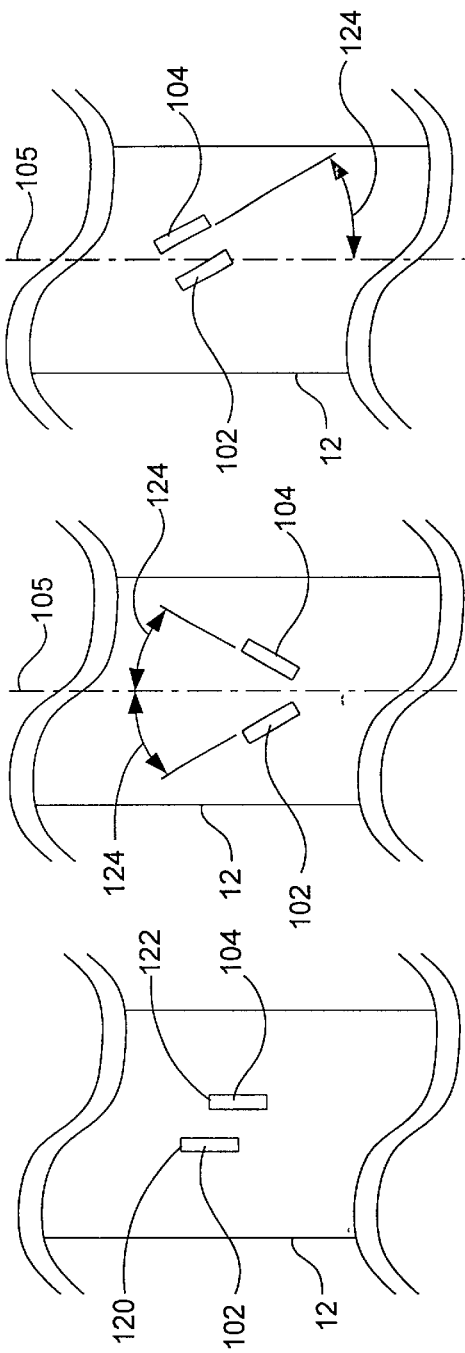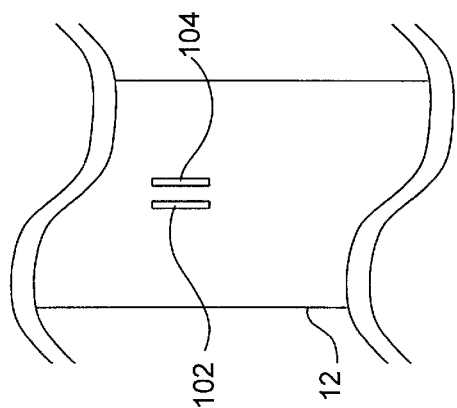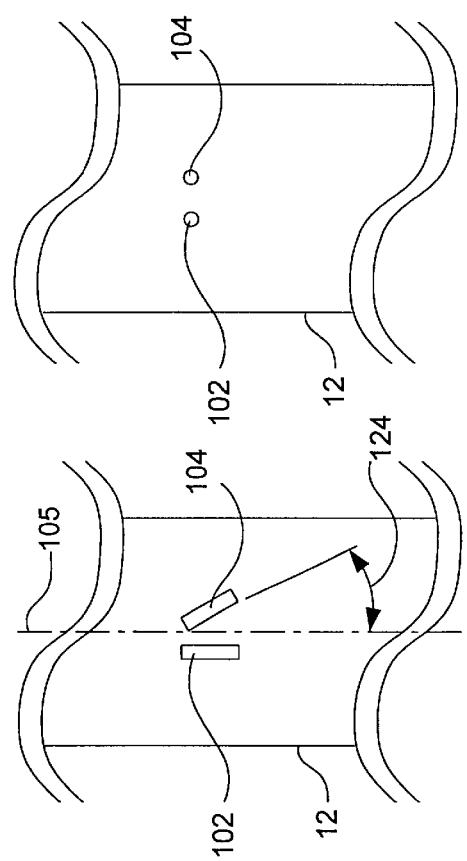

MICROWAVE ABLATION INSTRUMENT WITH A DIRECTIONAL RADIATION PATTERN

BACKGROUND OF THE INVENTION

The present invention relates generally to ablation devices that use electromagnetic energy to ablate internal biological tissues. More particularly, the present invention relates to an improved antenna arrangement for controlling the direction of energy delivered to a biological tissue during ablation.

Medical ablation devices have been around for some time. For example, ablation catheters utilizing electromagnetic energy, in both the RF and microwave frequency ranges, have been introduced and employed to various degrees to ablate biological tissues. One common application is to ablate myocardium tissues to treat a variety of cardiac arrhythmias. By way of example, representative microwave ablation catheters are described in the U.S. Pat. Nos. 4,641,649 to Walinsky; U.S. Pat. No. 5,246,438 to Langberg; and U.S. Pat. No. 5,405,346 to Grundy, et al., each of which is incorporated herein by reference.

Most existing microwave ablation catheters contemplate the use of antennas that produce a peripherally extending field that surrounds the catheter. That is, the electromagnetic energy generated by the antenna is propagated laterally to the sides of the catheter relatively uniformly about the antenna region of catheter. Although such catheter designs work well for a number of applications, in many applications it would be desirable to provide a more directional field that concentrates most of the electromagnetic energy generated by the antenna in a predetermined direction.

There have been some efforts to provide catheters and/or other ablation instruments with more directional fields. By way of example, U.S. Pat. No. 5,800,494 to Campbell, et al. and co-pending U.S. application Ser. No. 09/333,747 to Berube (Sep. 23, 1999) describe a number of antenna designs that generate generally forward firing fields. Additionally, U.S. Pat. No. 5,314,466 to Stern, et al, and co-pendingf U.S. application Ser. No. 09/178,066 to Berube, et al. (Jun. 14, 1999) describe antenna designs that generate generally side firing fields. Although such designs work well, there are continuing efforts to improve antenna designs to provide ablation instruments with specific directional components, such as in a lateral direction to one side of the catheter.

During positioning and/or use of the ablation catheter, it is often desirable to monitor certain electrophysiological properties of the heart. To facilitate such electrophysiological monitoring, electrodes are often positioned near the distal end of the catheter. Typically, such electrodes take the form of annular metallic rings. However, in some implementations, the annular rings have been replaced with electrode bands with multiple electrodes per band. By way of example, U.S. Pat. No. 5,788,692 to Campbell, et al. describes a mapping catheter with split electrode bands. Although the existing electrode designs work well, there are continuing efforts to improve their functionality.

SUMMARY OF THE INVENTION

To achieve the foregoing and other objects of the invention, an improved antenna arrangement for use in ablation devices is described. The described antenna arrangement is capable of creating an electromagnetic field, which extends to one side of the ablation device. The antenna arrangement includes an antenna and a reflector, which is positioned on a first side of the antenna. The antenna and the reflector are coupled to a suitable transmission line. The antenna and reflector cooperate to direct the majority of the resultant electromagnetic field in a predetermined direction to a second side of the antenna that is opposite the reflector.

The described antenna structure can be used in a wide variety of ablation devices including catheters and various other surgical instruments, which are generally used in procedures relating to the ablation of internal biological tissues. For example, they can be used to ablate tissues in the heart (e.g., cardiac), the brain(e.g., cerebral), the prostate, the stomach, the intestines, the liver and the like.

In some preferred embodiments, the reflector has a substantially arcuate shape that flares towards the antenna. By way of example, reflectors having arc angles in the range of approximately 90 to about 180 degrees work well. Additionally, the reflector is offset from, and extends in parallel to, the antenna. In embodiments that utilize a co-axial cable as the transmission line, the reflector is preferably coupled to the shield portion of the coaxial transmission line.

In some embodiments, the reflector and the antenna extend substantially in parallel longitudinally from the transmission line. In a related embodiment, the distal end of the reflector extends longitudinally to about the distal end of the antenna In some embodiments, the longitudinal axis of the antenna is offset from the longitudinal axis of the transmission line in a direction away from the reflector. In other embodiments, an impedance matching device is provided to increase the radiation efficiency of the antenna.

DESCRIPTION OF THE DRAWINGS

The present invention is illustrated by way of example, and not by way of limitation, in the figures of the accompanying drawings and in which like reference numerals refer to similar elements and in which:

FIG. 3 is an enlarged, side elevation view, in cross section, of the antenna arrangement of FIG. 2.

FIG. 4 is a front elevation view of the antenna arrangement taken substantially along the plane of the line 4—4' in FIG. 3.

FIG. 6 is an enlarged, bottom elevation view, in partial cross section, of the antenna arrangement of FIG. 2

FIGS. 7A & 7B are front elevation views of the electrode arrangement taken substantially along the plane of the line 7–7' in FIG. 6.

FIGS. 8A–8F show the electrode arrangement, in accordance with several embodiments of the present invention.

DETAILED DESCRIPTION OF INVENTION

Some specific embodiments of the invention are described below with reference to FIGS. 1–9. However, those skilled in the art will readily appreciate that the detailed description given herein with respect to these figures is for explanatory purposes as the invention extends beyond these limited embodiments. For example, for the purposes of illustration, the invention will be described in terms of a coronary microwave ablation catheter. However, it is contemplated that the invention may be implemented in any suitable ablation device including other types of catheters and surgical tools. Further, although the invention will be described in the context of microwave abalation devices, its may also be applied to ablation devices that used electromagnetic energy outside of the microwave frequency range (as for example, RF devices).

Figure 1:
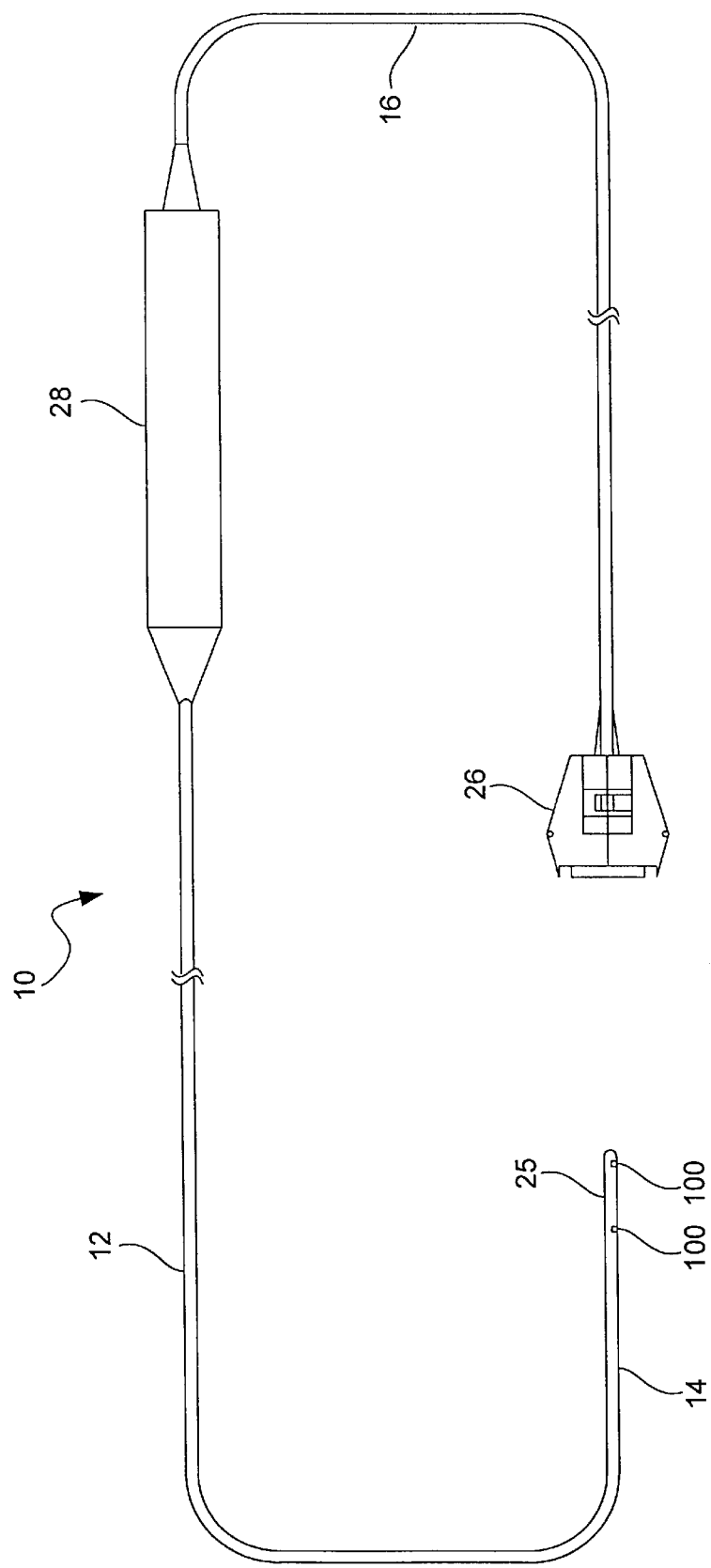
FIG. 1 is a top plan view of a catheter ablation system, in accordance with one embodiment of the present invention
Figure 2:
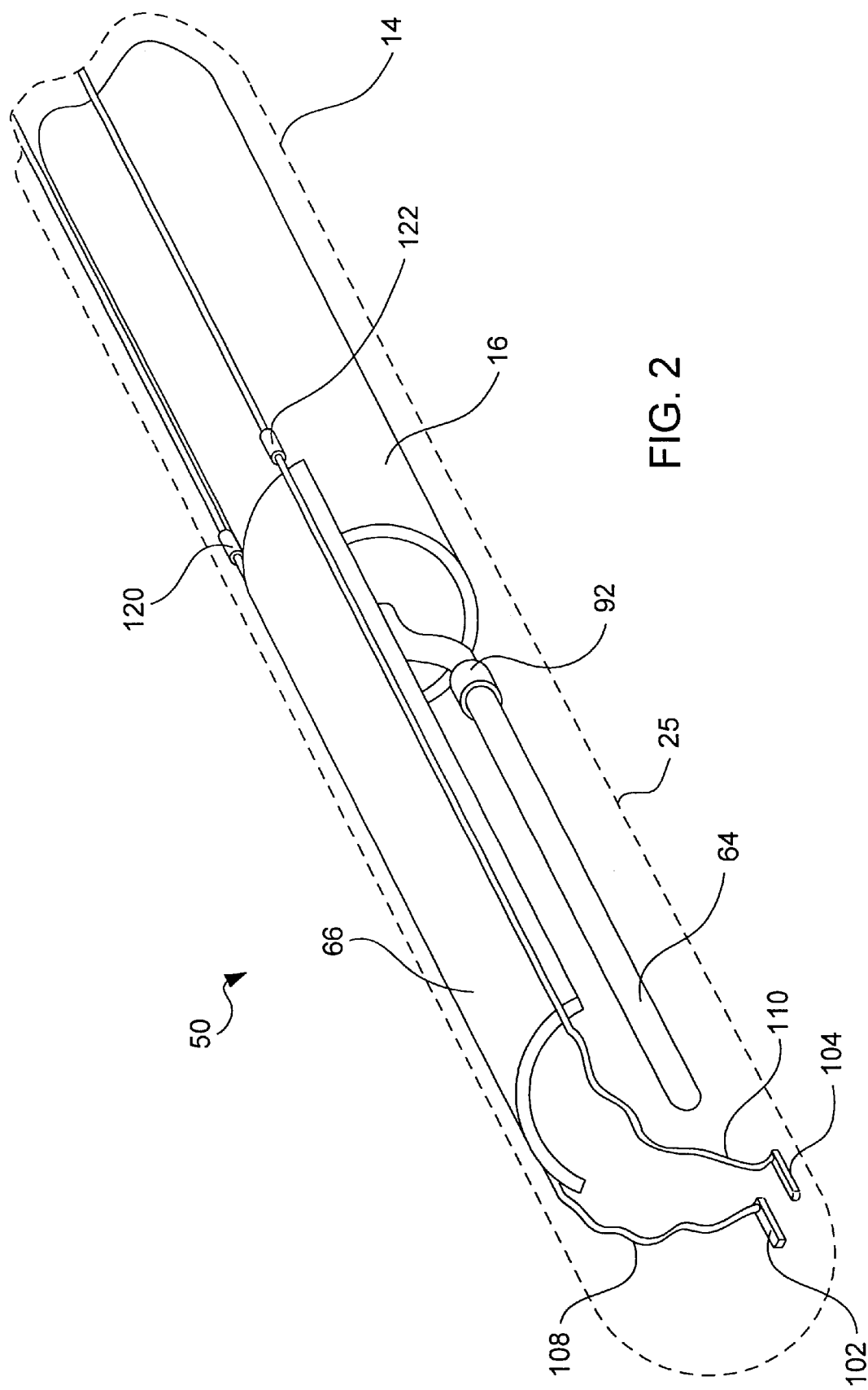
FIG. 2 is a perspective view of an antenna arrangement, in accordance with one embodiment of the present invention.

Referring initially to FIGS. 1–3, an ablation catheter system 10 generally includes an elongated catheter 12, which is designed for insertion into a vessel (such as a blood vessel) in the body of a patient. The catheter 12 typically includes a flexible outer tubing 14 (having one or several lumen therein), a transmission line 16 that extends through the flexible tubing 14 and an antenna 64 coupled to the distal end of the transmission line 16. The flexible outer tubing 14 may be made of any suitable material such as medical grade polyolefins, fluoropolymers, or polyvinylidene fluoride. By way of example, PEBAX resins from Autochem of Germany have been used with success for the outer tubing of the body of the catheter.

The transmission line 16 is arranged for actuating and/or powering the antenna 64. Typically, in microwave devices, a coaxial transmission line is used, and therefore, the transmission line 16 includes an inner conductor 20, an outer conductor 22, and a dielectric material 24 disposed between the inner and outer conductors. In most instances, the inner conductor 20 is coupled to the antenna 64. Further, the antenna 64 is typically enclosed (e.g., encapsulated) by an antenna enclosure 25 that is attached to the flexible outer tubing 14. The antenna enclosure 25 may be made of any suitable dielectric material such as medical grade epoxy, polyethylene and Teflon type products. The antenna enclosure 25 is used to remove the high electromagnetic field concentration present when an exposed metallic part of the antenna is in direct contact with the tissue to ablate.

Moreover, the proximal end of the transmission line 16 is typically coupled to a connector 26 that is suitable for connection to an electromagnetic energy source (not shown). A handle 28 may also be provided for use by the surgeon to facilitate steering and potentially other control functions. Additionally, the catheter 12 may include a variety of sensors for monitoring the patient during insertion, positioning and/or use of the catheter. By way of example, such sensors may include one or more electrodes 100 and one or more thermocouple wires (not shown).

In one embodiment, the electromagnetic power source (not shown) includes a microwave generator, which may take any conventional form. When using microwave energy for tissue ablation, the optimal frequencies are generally in the neighborhood of the optimal frequency for heating water. By way of example, frequencies in the range of approximately 800 MHz to 6 GHz work well. Currently, the frequencies that are approved by the FCC (Federal Communication Commission) for experimental clinical work are 915 MHz and 2.45 GHz. Therefore, a microwave generator having the capacity to generate microwave energy at frequencies in the neighborhood of 2.45 GHz may be chosen.

At the time of this writing, solid state microwave generators in the 1–3 GHz range are expensive. Therefore, a conventional magnetron of the type commonly used in microwave ovens is utilized as the generator. It should be appreciated, however, that any other suitable electromagnetic power source could be substituted in its place, and that the explained concepts may be applied at other frequencies.

In accordance with one aspect of the present invention, an antenna arrangement is provided that is arranged to direct a majority of an electromagnetic field to one side of the antenna and thus to one side of the catheter. The antenna arrangement preferably includes an antenna for generating an electromagnetic field, and a reflector for redirecting a portion of the electromagnetic field to one side of the antenna opposite the reflector. Correspondingly, a resultant electromagnetic field including a portion of the generated and a portion of the redirected electromagnetic field is directed in a desired direction. The use of a directional field has several potential advantages over conventional antenna structure that generate uniform fields about the catheter tip. For example, by forming a concentrated and directional electromagnetic field, deeper penetration of biological tissues may be obtained during ablation and the biological tissue targeted for ablation may be ablated without heating as much of the surrounding tissues and/or blood. Further, since the radiated power is not lost in the blood, less power is generally required from the power source, and less power is generally lost in the transmission line. Additionally, this arrangement may be used to form linear lesions that are more precise.

Referring to FIGS. 2–4, an antenna arrangement 50 configured for generating a concentrated electromagnetic field in a predetermined direction will be described in detail. The antenna arrangement 50 includes an antenna 64 configured for transmitting an electromagnetic field and a reflector 66 for redirecting a portion of the transmitted electromagnetic field. The proximal end 70 of the antenna 64 may be coupled directly or indirectly to the inner conductor 20 of the coaxial transmission line 16. A direct connection between the antenna 64 and the inner conductor 20 may be made in any suitable manner such as soldering, brazing, ultrasonic welding or adhesive bonding. In other embodiments, antenna 64 can be formed from the inner conductor 20 of the transmission line 16 itself. This is typically more difficult from a manufacturing standpoint but has the advantage of forming a more rugged connection between the antenna and the inner conductor. As will be described in more detail below, in some implementations, it may be desirable to indirectly couple the antenna to the inner conductor through a passive component in order to provide better impedance matching between the antenna arrangement and the coaxial transmission line.

In the illustrated embodiment, the antenna 64 is a longitudinally extending antenna that is laterally offset from the inner conductor 20 to put it closer to the edge of the antenna enclosure 25. The antenna shown is a simple longitudinally extending wire that extends distally (albeit laterally offset) from the inner conductor. However it should be appreciated that a wide variety of other antenna geometries may be used as well. By way of example, helical coils, flat printed circuit antennas and other antenna geometries will work as well.

As will be appreciated by those familiar with antenna design, the electromagnetic field generated by the illustrated antenna will be roughly consistent with the length of the antenna. That is, the area where the electromagnetic field is radiated is generally constrained to the longitudinal length of the antenna wire. Therefore, the length of the lesion created by the ablation element may be adjusted by adjusting the length of the antenna. Accordingly, catheters having specified ablation characteristics can be fabricated by building catheters with different length antennas. Additionally, it should be understood that longitudinally extending antennas are not a requirement and that other shapes and configurations may be used.

The antenna 64 is preferably formed from a conductive material. By way of example, spring steel, beryllium copper, or silver plated copper work well. Further, the diameter of the antenna 64 may vary to some extent based on the particular application of the catheter and the type of material chosen. By way of example, in microwave systems using a simple exposed wire type antenna, wire diameters between about 0.25 mm to about 0.50 mm work well. In the illustrated embodiment, the diameter of the antenna is about 0.325 mm.

In a preferred embodiment, the antenna 64 is positioned closer to the area designated for tissue ablation in order to have good energy transmission between the antenna and the tissue to be ablated. This is best achieved by placing the antenna 64 proximate to the outer peripheral surface of the antenna enclosure 25. More specifically, a longitudinal axis 74 of the antenna 64 is preferably off-set from, but parallel to, a longitudinal axis 76 of the inner conductor 20 in a direction away from the reflector 66 and therefore towards the concentrated electromagnetic field. By way of example, placing the antenna between about 0.125 to about 0.50 mm away from the outer peripheral surface of the antenna enclosure works well. In the illustrated embodiment, the antenna is about 0.375 mm away from the outer peripheral surface of the antenna enclosure 25. However, it should be noted that this is not a requirement and that the antenna position may vary according to the specific design of each catheter.

Referring now to the reflector 66, the reflector 66 is positioned laterally to a first side 86 of the antenna 64 and is configured to redirect a portion of the electromagnetic field that is transmitted towards the reflector 66 to a second side 88 of the antenna 64 opposite the reflector 66. Correspondingly, a majority of the electromagnetic field is directed away from the second side 88 of the antenna 64. Furthermore, the reflector 66 is disposed substantially parallel to the antenna 64 to provide better control of the electromagnetic field during ablation.

Unwanted coupling between the antenna 64 and the reflector 66 may occur if the reflector is too close to the antenna 64. Therefore, the reflector 66 is off-set from the antenna 64. It has been found that the minimum distance between the reflector and the antenna may be between about 0.50 to about 0.75 mm, in the described embodiment, in order to reduce the coupling. However, the distance may vary according to the specific design of each catheter system.

The proximal end 78 of the reflector 66 is preferably coupled to the outer conductor 22 of the coaxial transmission line 16. Connecting the reflector to the outer conductor serves to better define the electromagnetic field generated during use. That is, the radiated field is better confined along the antenna, to one side, when the reflector is electrically connected to the outer conductor of the coaxial transmission line. The connection between the reflector 66 and the outer conductor 22 may be made in any suitable manner such as soldering, brazing, ultrasonic welding or adhesive bonding. In other embodiments, the reflector can be formed from the outer conductor of the transmission line itself. This is typically more difficult from a manufacturing standpoint but has the advantage of forming a more rugged connection between the reflector and the outer conductor. In other embodiments, the reflector may be directly coupled to a ground source or be electrically floating.

As previously noted, the antenna 64 typically emits an electromagnetic field that is fairly well constrained to the length of the antenna. Therefore, in some embodiments, the distal end 80 of the reflector 66 extends longitudinally to about the distal end 72 of the antenna 64 so that the reflector can effectively cooperate with the antenna. This arrangement serves to provide better control of the electromagnetic field during ablation. However, it should be noted that the actual length of the reflector may vary according to the specific design of each catheter. For example, catherers having specified ablation characteristics can be fabricated by building catheters with different length reflectors.

Furthermore, the reflector 66 is typically composed of a conductive, metallic mesh or foil. One particularly suitable material is silver plated copper, for example, having a thickness in the range of about 0.05 mm to about 0.125 mm. In the illustration shown, the thickness is about 0.075 mm. Another suitable arrangement may be a stainless steel mesh or foil that has a layer of silver formed on its inner peripheral surface. However, it should be understood that these materials are not a limitation. Furthermore, the actual thickness of the reflector may vary according to the specific material chosen.

Referring to FIG. 4, the reflector 66 is configured to have an arcuate or meniscus shape (e.g., crescent), with an arc angle 90 that opens towards the antenna 64. Flaring the reflector 66 towards the antenna 64 serves to better define the electromagnetic field generated during use. The arc angle 90 is typically configured between about 90° to about 180°. By way of example, an arc angle of about 120° works well. Additionally, it has been found that if the arc angle 90 is greater than 180° the radiation efficiency of the antenna arrangement decreases significantly.

Furthermore, while the reflector 66 is shown and described as having an arcuate shape, it will be appreciated that a plurality of forms may be provided to accommodate different antenna shapes or to conform to other external factors necessary to complete a surgical procedure. For example, any flared shape that opens towards the antenna 64 may work well, regardless of whether it is curvilinear or rectilinear.

Further still, it should be noted that the shape of the reflector 66 need not be uniform. For example, a first portion of the reflector 66 (e.g., distal) may be configured with a first shape (e.g., 90° arc angle) and a second portion (e.g., proximal) of the reflector 66 may be configured with a second shape (e.g., 120° arc angle). Varying the shape of the reflector 66 in this manner may be desirable to obtain a more uniform radiated field. While not wishing to be bound by theory, it is generally believed that the energy transfer between the antenna and the tissue to be ablated tends to increase by decreasing the coverage angle of the reflector, and conversely, the energy transfer between the antenna and the tissue to be ablated tends to decrease by increasing the coverage angle of the reflector. Accordingly, the shape of the reflector may be altered to balance out non-uniformities found in the radiated field of the antenna arrangement.

It should also be noted that the longitudinal length of the reflector 66 need not be uniform. That is, a portion of the reflector 66 may be stepped towards the antenna 64 or a portion of the reflector 66 may be stepped away from the antenna 64. Stepping the reflector in this manner may be desirable to obtain a more uniform radiated field. While not wishing to be bound by theory, it is believed that by placing the reflector closer to the antenna, a weaker radiated field may be obtained, and that by placing the reflector further away from the antenna, a stronger radiated field may be obtained. Accordingly, the longitudinal length of the reflector may be altered to balance out non uniformities found in the radiated field of the antenna arrangement.

In a typical microwave ablation catheter system, it is important to match the impedance of the antenna with the impedance of the transmission line. As is well known to those skilled in the art, if the impedance is not matched, the catheter's performance tends to be well below the optimal performance. The decline in performance is most easily seen in an increase in the reflected power. Therefore, the system is typically designed to provide a set impedance. By way of example, a typical set impedance of the catheter system may be on the order of 50 ohms.

Referring back to FIGS. 2 & 3 and in accordance with one embodiment of the present invention, an impedance matching device 92 may be provided to facilitate impedance matching between the antenna 64 and the transmission line 16. The impedance matching device 92 is generally disposed proximate the junction between the antenna 64 and the inner conductor 20. For the most part, the impedance matching device 92 is configured to place the antenna structure in resonance to minimize the reflected power, and thus increase the radiation efficiency of the antenna structure.

In one embodiment, the impedance matching device is determined by using a Smith Abacus Model. In the Smith Abacus Model, the impedance matching device may be ascertained by measuring the impedance of the antenna with a network analyzer, analyzing the measured value with a Smith Abacus Chart, and selecting the appropriate device. By way of example, the impedance matching device 92 may be any combination of a capacitor, resistor, inductor, stub tuner or stub transmission line, whether in series or in parallel with the antenna. An example of the Smith Abacus Model is described in Reference: David K. Cheng, "Field and Wave Electromagnetics," second edition, Addison-Wesley Publishing, 1989, which is incorporated herein by reference. In one preferred implementation, the impedance matching device is a serial capacitor having a capacitance in the range of about 0.6 to about 1 picoFarad. In the illustration shown, the serial capacitor has a capacitance of about 0.8 picoFarad.

As can be seen from the foregoing, the advantages of the antenna arrangement are numerous. Different embodiments or implementations may have one or more of the following advantages. One advantage of the antenna arrangement is that a more directional electromagnetic field is produced. Since a greater part of the radiated energy is directed to the tissue to ablate, deeper lesions can be produced for the same amount of radiated power. In addition, since the energy is not lost in the blood, the output power requirements from the generator is decreased. In other words, the antenna arrangement uses less energy to produce the tissue ablation. Accordingly, the size of the transmission line (e.g., coaxial cable) may be decreased, which as a result may reduce the overall size of the catheter or provide more space for the steering system or other components.

Another advantage of the antenna arrangement is that the energy is distributed with greater accuracy, and with less dispersion than a conventional antenna without a reflector. That is, the antenna arrangement provides an electromagnetic field with a directional component that extends to one side of the catheter. Tissue ablation can thus be more strategically controlled, directed and performed without concern for undesirable ablation of other adjacent tissues and/or blood which may otherwise be within range of the electromagnetic energy propagating from the antenna. In other words, any tissues and/or blood which are out of the line of sight of the directional field will not be subjected to the electromagnetic field and thus not be ablated.

Figure 5A:
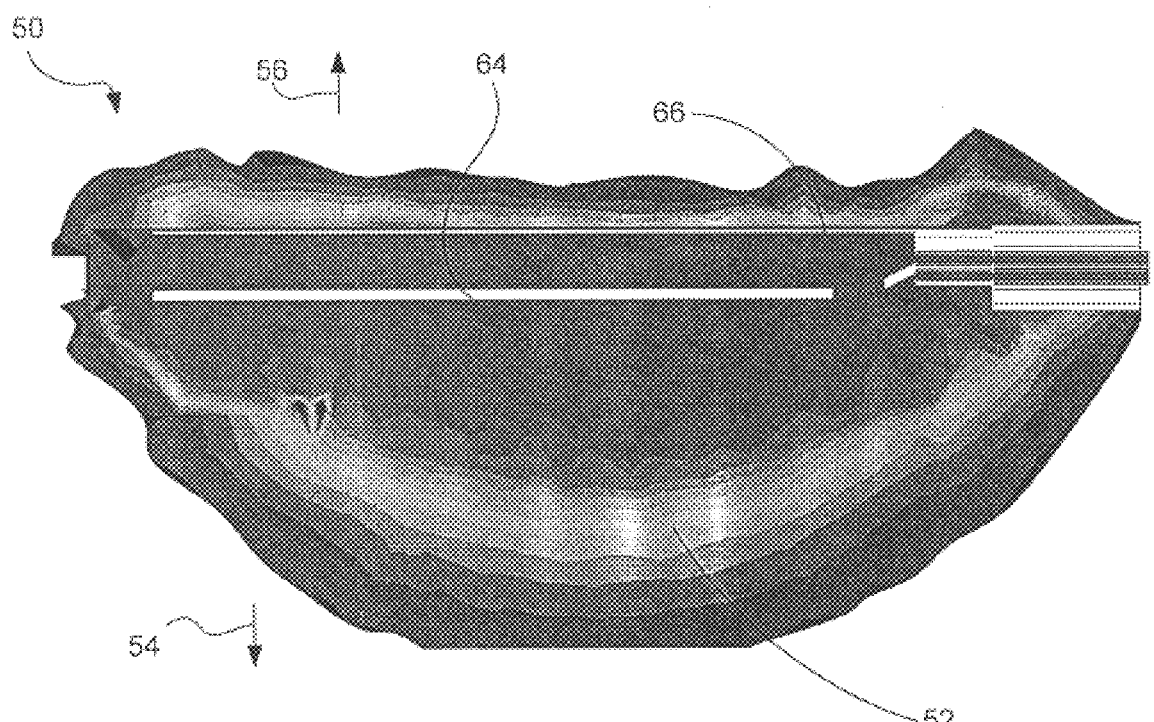
FIG. 5A is a side cross sectional view of the antenna arrangement of FIG. 2 while it is generating a concentrated electromagnetic field in a predetermined direction.
Figure 5B:
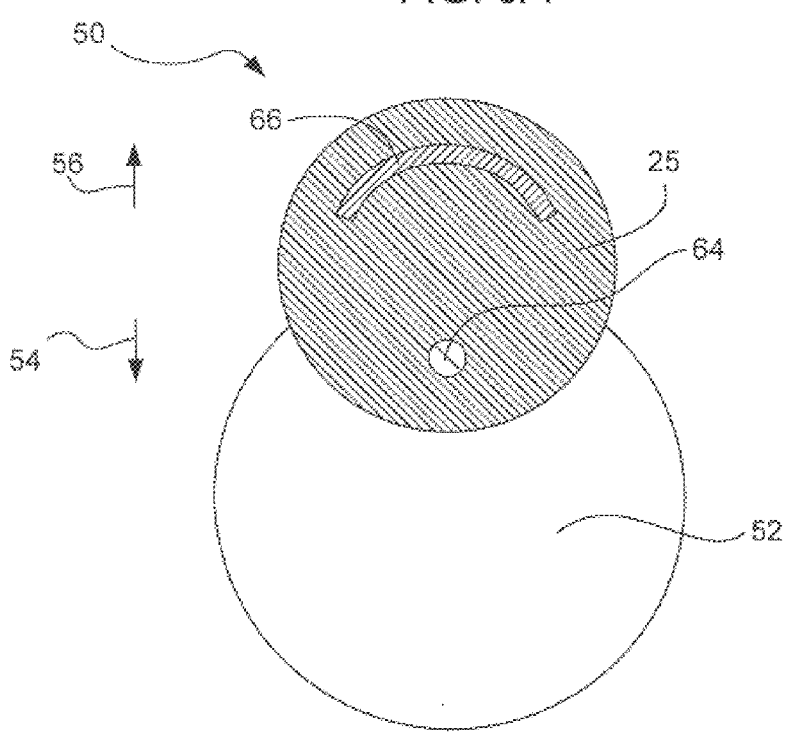
FIG. 5B is a front cross sectional view of FIG. 2 while it is generating a concentrated electromagnetic field in a predetermined direction.

To better illustrate the advantages, FIGS. 5A & 5B illustrate the electromagnetic field 52 produced by the aforementioned antenna arrangement 50 (FIG. 5A is a side cross section view and FIG. 5B is a front cross section view). As shown, the antenna arrangement 50, including the antenna 64 and reflector 66, provides an electromagnetic field pattern 52 that maximizes the field strength at the antenna side 54 of the arrangement and minimizes the field strength at the reflector side 56 of the arrangement.

When using directional fields such as these, it is important to provide a mechanism for aligning the directional field with the tissue targeted for ablation in order to prevent the unwanted ablation of tissues and fluids. If the directional field is not aligned correctly, for example, the energy may radiate into surrounding tissues and fluids rather than into the targeted tissue. Therefore, in accordance with another aspect of the present invention, a positioning electrode is provided to measure the electrical activity (or electrophysiological signals) of biological tissues proximate to one side of the catheter. The positioning electrode is configured to inform a surgeon that one side of the catheter is in contact with a biological tissue. In this manner, a surgeon may determine if the directional component of the electromagnetic field is aligned with the targeted tissue. Additionally, the positioning electrode may be used to map the biological tissue prior to or after an ablation procedure, as well as be used to monitor the patient's condition during the ablation process.

To facilitate discussion of the above aspects of the present invention, FIGS. 2, 6 7A & 7B illustrate a positioning electrode arrangement 100 configured for sensing electrical activity in substantially one direction, in accordance with one aspect of the present invention. In FIG. 6, a portion of the antenna enclosure 25 has been removed between the antenna 64 and the reflector 66 to better show the features of the invention. The electrode arrangement 100 generally includes a pair of longitudinally extending electrode elements 102 and 104 that are disposed on the outer periphery of the antenna enclosure 25. The pair of electrode elements 102, 104 are positioned side by side and arranged to be substantially parallel to one another. Furthermore, the pair of electrode elements 102, 104 are arranged to be substantially parallel to the longitudinal axis 105 of the antenna enclosure 25. In general, splitting the electrode arrangement into a pair of distinct elements permits substantial improvements in the resolution of the detected electrophysiological signals. Therefore, the pair of electrode elements 102, 104 are preferably spaced apart and electrically isolated from one another.

As shown in FIG. 7A, the pair of electrodes 102, 104 are positioned along the outer perimeter of the antenna enclosure 25 and are separated by a pair of spaces 115, 117. The first space 115 has a first perimeter distance and the second space 117 has a second perimeter distance. As shown, the first space 115 is arranged to be smaller than the second space 117. This is preferably done to ensure that the electrode elements 102, 104 are sensing electrical activity in substantially the same direction. It is generally believed that too large a space may create problems in determining the directional position of the catheter and too small a space may degrade the resolution of the detected electrophysiological signals. In one implementation, the ratio of the second distance to the first distance is at most about 4 to 1. In most embodiments, however, the first space is much smaller. By way of example, a first distance of between about 0.5 and 2 mm works well for catheters having a diameter between about 2.3 mm and about 4.6 mm.

To elaborate further and as shown in FIG. 7B, the electrodes 102, 104 are arranged to have centerlines 106, 107, which extend radially from the longitudinal axis 105 of the antenna enclosure 25. As shown, the space between the centerlines are defined by angle A. Again, the angle A should be sufficiently small in order to ensure that the elements are sensing in substantially one direction. It should be additionally noted that a smaller angle is also preferred over a large angle because a large angle requires a greater pressure between the catheter and the tissue to ensure proper electrode contact. By way of example, an angle between about 15 degrees to about 90 degrees, and more particularly less than about 45 degrees works well.

As shown in FIGS. 2 & 6, the electrode elements 102, 104 are positioned substantially proximate the distal end 72 of the antenna 64. Positioning the electrode elements in this location is believed to be particularly useful to facilitate mapping and monitoring as well as to position the catheter in the area designated for tissue ablation. For example, during some procedures a surgeon may need to ascertain where the distal end of the antenna is located in order to ablate the appropriate tissues. In another implementation, the electrode elements (102, 104) are positioned substantially proximate the proximal end 70 of the antenna 64. Although only two positions have been described, it should be understood that the electrode elements may be positioned in any suitable position along the length of the catheter. For example, the electrodes may be disposed on the flexible tubular member of the catheter, on the distal face of the antenna enclosure, or on the antenna enclosure between the distal and proximal ends of the antenna.

While not specifically shown, a plurality of electrode arrangements may be disposed along the catheter as well. By way of example, a first set of electrode elements may be disposed distally to the antenna arrangement and a second set of electrode elements may be disposed proximally to the antenna arrangement. The electrodes may also be used with other types of mapping electrodes, for example, a variety of suitable mapping electrode arrangements such as electrode bands which are well known in the art.

The electrode elements 102, 104 may be formed from any suitable material. By way of example, stainless steel and iridium platinum work well as the electrode materials. The width (or diameter) and the length of the electrode may vary to some extent based on the particular application of the catheter and the type of material chosen. Furthermore, the electrodes are preferably dimensioned to minimize electromagnetic field interference. In most embodiments, the electrodes are arranged to have a length that is substantially larger than the width. By way of example, an electrode having a width (or diameter) between about 0.25 mm and about 0.625 mm and a length between about 0.50 mm and about 1 mm works well. As should be appreciated, electrodes arranged in this manner are easier to assemble. However, it should be understood that this is not a requirement and that the length and width of the electrodes may vary according to the specific needs of each catheter.

Although the electrode arrangement has been shown and described as being parallel plates that are substantially parallel to the longitudinal axis of the antenna enclosure and aligned longitudinally with each other (e.g., distal and proximal ends match up), it should be noted that this is not a limitation and that the electrodes can be configured to be angled relative to the longitudinal axis of the antenna enclosure (or one another) or offset longitudinally with each other. Furthermore, although the electrodes have been shown and described as being a plate, it should be noted that the electrodes may be configured to be a wire or a point such as a solder blob. If a point is used, a point diameter between about 0.25 mm and about 0.5 mm works well.

Referring to FIGS. 8A–8F, a few variations of the aforementioned electrodes 102, 104 are shown on a segmented section of the catheter 12. By way of example, the segmented section may be a portion of the flexible outer tubing 14 or a portion of the antenna enclosure 25. In FIG. 8A, the electrodes 102, 104 are shown offset longitudinally such that the distal end 120 of the first electrode 102 is distally placed relative to the distal end 122 of the second electrode 104. In FIG. 8B, the electrodes 102, 104 are configured to be angled opposite to each other and relative to the longitudinal axis 105 of the catheter 12. As shown, an angle 124 describes this angular position. By way of example, an angle between about 0 degree and about 45 degrees works well. The electrodes 102, 104 can be configured to be angled distally outward (as shown) or angled distally inward. In FIG. 8C, the electrodes 102, 104 can be angled such that they remain parallel to one another. In FIG. 8D, one of the electrodes 104 is arranged to be angled relative to the longitudinal axis 105 of the catheter 12 while the other electrode 102 is arranged to be parallel to the longitudinal axis 105 of catheter 12. Additionally, in FIG. 18E, the electrodes 102, 104 are shown as point electrodes, and in FIG. 18F, the electrodes 102, 104 are shown as wire electrodes. It should be noted that in all of the described embodiments, the electrodes are preferably arranged to be adjacent one another.

Referring back to FIGS. 2 & 6, each of the electrode elements 102, 104 is electrically coupled to an associated electrode wire 108, 110, which extend through antenna enclosure 25 to at least the proximal portion of the flexible outer tubing 14. In most embodiments, the electrode wires 108, 110 are electrically isolated from one another to prevent degradation of the electrical signal. The connection between the electrodes 102, 104 and the electrode wires 108, 110 may be made in any suitable manner such as soldering, brazing, ultrasonic welding or adhesive bonding. In other embodiments, the longitudinal electrodes can be formed from the electrode wire itself. Forming the longitudinal electrodes from the electrode wire, or out of wire in general, is particularly advantageous because the size of wire is generally small and therefore the longitudinal electrodes elements may be positioned closer together thereby forming a smaller arrangement that takes up less space. As a result, the electrodes may be positioned almost anywhere on a catheter or surgical tool.

In some embodiments, the electrode material is printed on the catheter surface using known printed circuit techniques. In other embodiments, the electrode material is directly deposited on the catheter surface (antenna enclosure) using techniques such as chemical vapor deposition or ion implantation. One significant advantage of these techniques are that the electrodes themselves are essentially as flexible as the tubular member (antenna enclosure) and thus do not inhibit the catheter's maneuverability regardless of the electrode dimensions. This even further improves the maneuverability of the catheter tip and permits the use of electrodes of any desired size since it is relatively easy to control the electrode dimensions in these processes. Another significant advantage of these techniques are that the electrodes can be arranged with a wide variety of shapes. For example, the shape of the electrodes may be arranged to be linear, curvilinear, circular, rectangular, triangular, elliptical, non-uniform and the like. Further still, the shape of the first electrode may be configured with a first shape and the shape of the second electrode may be configured with a second shape.

For the most part, the information obtained from the electrodes 102, 104 are transmitted via electrode wires 108, 110, through the connector (not shown) and through the power supply (not shown) to external electronics such as an EP signal monitoring device. Filtering of the signal may be provided as necessary. In alternative embodiments, some of the external electronics could be incorporated into the power supply and/or the power supply could use information obtained from the electrodes in its control scheme.

Importantly, electrically coupling between the antenna arrangement 50 and the electrode arrangement 100 may occur if the electrode elements 102, 104 are positioned too close to the antenna 64. That is, the antenna may induce a current in the electrode elements, which may adversely effect the clarity of the electrophysiological signal. Furthermore, the coupling between the antenna 64 and the electrode wires 108, 110 may extend the radiation pattern along the electrode wires and the transmission line. As a result, the ablation pattern formed by the microwave catheter may no longer be confined along the antenna 64, but rather all along the distal part of the catheter 12. Several techniques can be implemented to reduce the coupling between the antenna 64 and the electrodes 102, 104. In some cases, the electrodes can be moved a distance away from the antenna. However, if the distance is too great then positioning and mapping will not be as effective. In other cases, a highly resistive electrode wire may be used to reduce the coupling between the electrodes and the antenna. However, as is well known to those skilled in the art, it is difficult and expensive to manufacture a highly resistive wire with a small diameter.

Therefore, in accordance with one embodiment of the present invention, a low impedance or highly conductive electrode wire is used along with a surface mount resistor to reduce the coupling between the antenna wires and the electrode wires. As shown in FIG. 2, a pair of surface mount resistors 120 and 122 are electrically coupled to each of the highly conductive electrode wires 108, 110. It is generally believed that the surface mount resistors 120, 122 provide a means for blocking (or knocking down) the electromagnetic coupling between the electromagnetic source (e.g., antenna) and the electrode wire 108, 110. That is, The surface mount resistors 120, 122 are very useful for reducing the microwave radiation along the electrode wires 108, 110. In this manner, the surface mount resistors allow a certain amount of control over the radiation pattern produced by the antenna. Furthermore, low impedance or highly conductive wires are fairly inexpensive and easy to manufacture. By way of example, electrode wires formed from stainless steel, having a diameter in the range of about 0.075 to about 0.025 mm work well. Of course, the diameter may vary according to the specific material chosen. Additionally, with regards to the surface mount resistors, a resistance between about 5 and about 20 kilo-ohms works well. In the illustration shown, the resistance of the resistor is about 15 kilo-ohms.

Moreover, even if the manufacturing of a highly resistive wire with a small diameter is challenging, some techniques already exist to produce it. The highly resistive wire can thus be used as the complete electrode wire or as a part of the electrode wire. The highly resistive wire is preferably used close to the microwave antenna in locations where the electromagnetic field is present. The highly resistive wire can be made by depositing, on a dielectric substrate, a thin layer of metallic material having a poor electrical conductivity such as tungsten. Since the resistance of the wire is inversely proportional to its cross-sectional area, the width and the thickness of the metallic deposition must be very small. As an example, a width of 0.25 mm and a thickness of 0.01 mm works well with tungsten. The highly resistive wire can also be made with a conductive polymer or a carbon fiber based material. In any case, the highly resistive wire in electrically connected to the electrode wires in order to be able to record the electrical activity of the tissue.

In a preferred embodiment, the electrode arrangement 100 is used to determine if the antenna arrangement 50 is in the proper position for ablation. That is, the electrode arrangement 100 is used to determine if the antenna arrangement 50, which has a directional component, is facing the right direction. As mentioned, the antenna arrangement 50 is arranged to work in a first predetermined direction laterally to one side of the catheter. The first predetermined direction generally extends radially from the longitudinal axis of the catheter. However, it should be noted that this is a vector direction (as shown in FIG. 5B) since the field generally covers a greater distribution than a single line. In this embodiment, the pair of spaced electrodes are carried by a portion of the catheter and positioned in a second predetermined direction, which also extends radially from the longitudinal axis of the catheter. The second predetermined direction is positioned relative to the first predetermined direction such that the electrodes 102, 104 provide a reference point for determining the radial position of the working antenna arrangement 50 with respect to sensed biological tissue. For instance, in order to determine if the working element is facing the correct tissue, the catheter 12 can be rotated around its principal axis (e.g., longitudinal axis 105) until the electrodes sense the electrical activity of a known tissue. As can be appreciated, this aspect of the invention is especially beneficial when the ablation device is hidden behind tissues, for example, during ablation of the posterior wall of the heart during an open-chest procedure.

In one embodiment, the second predetermined position is in substantially the same direction as the first predetermined direction. More specifically, the electrode arrangement is positioned to sense electrical activity in a direction that coincides with the direction of the electromagnetic field produced by the antenna arrangement. Referring to FIGS. 2, 3, 6 & 7, the electrode elements 102, 104 are disposed on the antenna enclosure 25 so that they are substantially aligned with the longitudinal axis 74 of the antenna 64 and the middle 84 of the reflector 66. Further, the electrode elements 102, 104 are disposed on the antenna side 54 of the antenna enclosure opposite the reflector 66. As a result, the electrode elements tend to be substantially aligned with the directional electromagnetic field produced by the antenna arrangement, and therefore, they can be used to ensure that the directional electromagnetic field is ablating in the direction of the targeted biological tissues.

Although the electrodes are shown and described as being substantially aligned with the directional component of the antenna arrangement, it should be noted that the electrodes may be positioned at other radial positions about the catheter. For example, the electrodes may be positioned opposite the directional component. That is, the electrodes may be disposed on the side of the reflector that is opposite the antenna. This type of arrangement may be necessary to protect a structure such as a nerve or part of the brain. As can be appreciated, the electrodes provide a reference point on the catheter relative to the tissues being sensed.

Furthermore, the electrode wires 108, 110 are configured to extend through the antenna enclosure in a manner that reduces the unwanted coupling between the electrode wires and the antenna when the antenna is activated. In particular, the electrode wires 108, 110 are configured to extend orthogonally through the antenna enclosure 25 from the electrode elements 102, 104 to the distal end of the reflector 66 and longitudinally through the antenna enclosure 25 from the distal end of the reflector 66 to at least the proximal end of the reflector 66. The electrode wires 108, 110 are also positioned away from the antenna 64 and to the reflector side 56 of the antenna enclosure such that the reflector 66 is disposed between the electrode wires 108, 110 and the antenna 64 (e.g., behind the reflector). Accordingly, the reflector 66 tends to electrically shield the electrode wires 108, 110 from the antenna 64. That is, there is substantially no coupling between the electrode wires 108, 110 and the antenna 64 between the distal end 80 of the reflector 66 and the proximal end 78 of the reflector 66, and therefore the electrical signals tend to have improved resolution. Additionally, the microwave energy emitted by the antenna 64 stays well confined along the antenna portion and the quality of the electrical signals measured by the electrodes stay adequate.

Also shown in FIG. 2, the surface mount resistors 120, 122 are disposed at the proximal end 78 of the reflector 66. However, it is generally believed that the closer the surface mount resistors are to the coupling source, the more effective they tend to be at reducing the coupling. Therefore, in other embodiments, the surface mount resistors may be disposed along the longitudinal length of the reflector.

In an alternate embodiment of the present invention, the electrode arrangement 100 is arranged to measure the impedance between the pair of electrodes to assess the orientation of the working member (e.g. antenna arrangement). In this embodiment, an initial current is supplied to one the electrodes and returned by the other electrode. During this process, the voltage (V) is measured across the two electrodes, as well as the initial current (I). The inter electrode impedance is thus proportional to the ratio of voltage to current (V/I). While not wishing to be bound by theory, it is generally believed that different mediums connecting the electrodes tend to generate different impedances. For example, when the electrodes are in the air, the inter-electrode impedance is very high and when the electrodes are simultaneously touching the tissue the inter electrode impedance is low. Accordingly, the position of the electrode arrangement with respect to adjacent tissues can be ascertained by repositioning the catheter until a known or desired impedance is found. Because the position of the working member is known relative to the position of the electrodes, the working member may be properly directed towards the targeted tissue.

Another requirement of most catheters is that some type of steering mechanism must be provided to permit the physician to direct the antenna portion of the catheter to the proper location. In one particular type of steering, the catheter is positioned proximate to the targeted tissue, and the steering system is actuated to move the antenna arrangement adjacent to the targeted tissue. If the antenna arrangement is properly positioned then the electrode elements tend to have a very sharp signal, and therefore, the tissue may be ablated by the antenna arrangement. Steering mechanisms are well known in the art and for the sake of brevity will not be described in detail.

As can be seen from the foregoing, the advantages of the electrode arrangement are numerous. Different embodiments or implementations may have one or more of the following advantages. One advantage of the electrode arrangement is that the position of one side of the catheter can be determined by a surgeon. As a result, a surgeon may manipulate the catheter to ensure that it is in the proper position for ablation. Accordingly, the energy for ablating can be directed towards the targeted tissue rather than the surrounding tissue. This is especially important when the electromagnetic field is emitted in substantially one direction. Another advantage of the electrode arrangement is that the electrodes do not take up a lot of space, and therefore may placed at positions that may not have been accessible with prior art electrodes.

Those skilled in the art will readily appreciate that the detailed description of the electrode arrangement given herein with respect to figures is for explanatory purposes as the invention extends beyond these limited embodiments. For example, although the invention was described in terms of the previously described microwave ablation catheter, it is contemplated that the invention may be practiced in any suitable ablation catheter, as well as other suitable ablation devices (e.g., surgical tools). Note that the above is true, irrespective of whether the electromagnetic field generated by the device is directional (e.g., side or front of a catheter) or non-directional (e.g., peripherally extending field) or whether the frequency of the electromagnetic field is in the microwave spectrum or other spectrums such as infrared, visible, ultraviolet and the like. Furthermore, it is contemplated that ablative energies other than that which is formed by electromagnetic fields may be used along with the described electrode arrangement. By way of example, lasers, cryogenics, ultrasound pressure waves, radiofrequency currents and the like may be used. Moreover, it is contemplated that the electrode arrangement may be used in any working member that is arranged to work in a predetermined direction laterally to one side of a catheter or surgical tool. By way of example, the working member may be a drug delivery device, a specimen retrieval device, a spatial marker, and/or the like.

In one embodiment, the described catheter is used for abalating cardiac tissues. Several cardiac procedures will now be discussed. These procedures are generally well known in the art and for the sake of brevity will not be described in detail. Furthermore, it should be understood that the present invention is not limited by these particular procedures and that the present invention may be applied in other areas of the heart as well. In one implementation, the catheter is used to ablate the isthmus between the tricuspid valve and the inferior vena cava of a heart in order to treat type 1 atrial flutter. In another implementation, the catheter is used to create linear lesions between any of the pulmonary veins of the heart in order to treat atrial fibrillation. In yet another implementation, the catheter is used to create linear lesions on the posterior or lateral wall of the right atrium, from the superior to the inferior vena cava of the heart in order to treat type II atrial flutter and/or atrial fibrillation.

In a further implementation, the catheter is used in the right atrium to ablate the isthmus between the inferior caval vein to treat type 1 flutter. In another implementation, the catheter is used in the right atrium to ablate the lateral right free wall between the superior and the inferior caval veins to treat atypical flutter. In yet another implementation, the catheter is used in the right atrium to produce an ablation from the cristae terminallis to the oval fossae to stop any of the macro-reentry circuits in the right atrium. In an additional implementation, the catheter is used to ablate the posterior wall of the left atrium to produce an ablation to link any of the pulmonary veins together to treat one of paroxysmal, recurrent atrial fibrillation and chronic atrial fibrillation. In another implementation, the catheter is used to ablate the posterior wall of the left atrium to produce an ablation to link any of the superior pulmonary veins to the entrance of the left appendage to avoid any of the macro reentry circuits in the left atrium. In yet another implementation, the catheter is used to ablate the ventricular wall to treat ventricular tachycardia.

In another implementation, the catheter is used epicardially to electrically isolate the superior and inferior right pulmonary veins from the atrium to treat one of paroxysmal, recurrent atrial fibrillation, and chronic atrial fibrillation. In another implementation, the catheter is used epicardially to electrically isolate the superior and inferior left pulmonary veins from the atrium to treat one of paroxysmal, recurrent atrial fibrillation, and chronic atrial fibrillation. In another implementation, the catheter is used epicardially and introduced along the transverse sinus to produce an ablation between the left and right superior pulmonary veins to treat on of paroxysmal, recurrent atrial fibrillation, or chronic atrial fibrillation. In yet another implementation, the catheter is used epicardially to produce an ablation between one of the left pulmonary veins to the left appendage to avoid any macro reentry circuits in the left atrium. In an additional implementation, the catheter is used epicardially to produce an ablation between the superior and inferior caval veins to avoid any macro reentry circuits in the right atrium.

Figure 9:
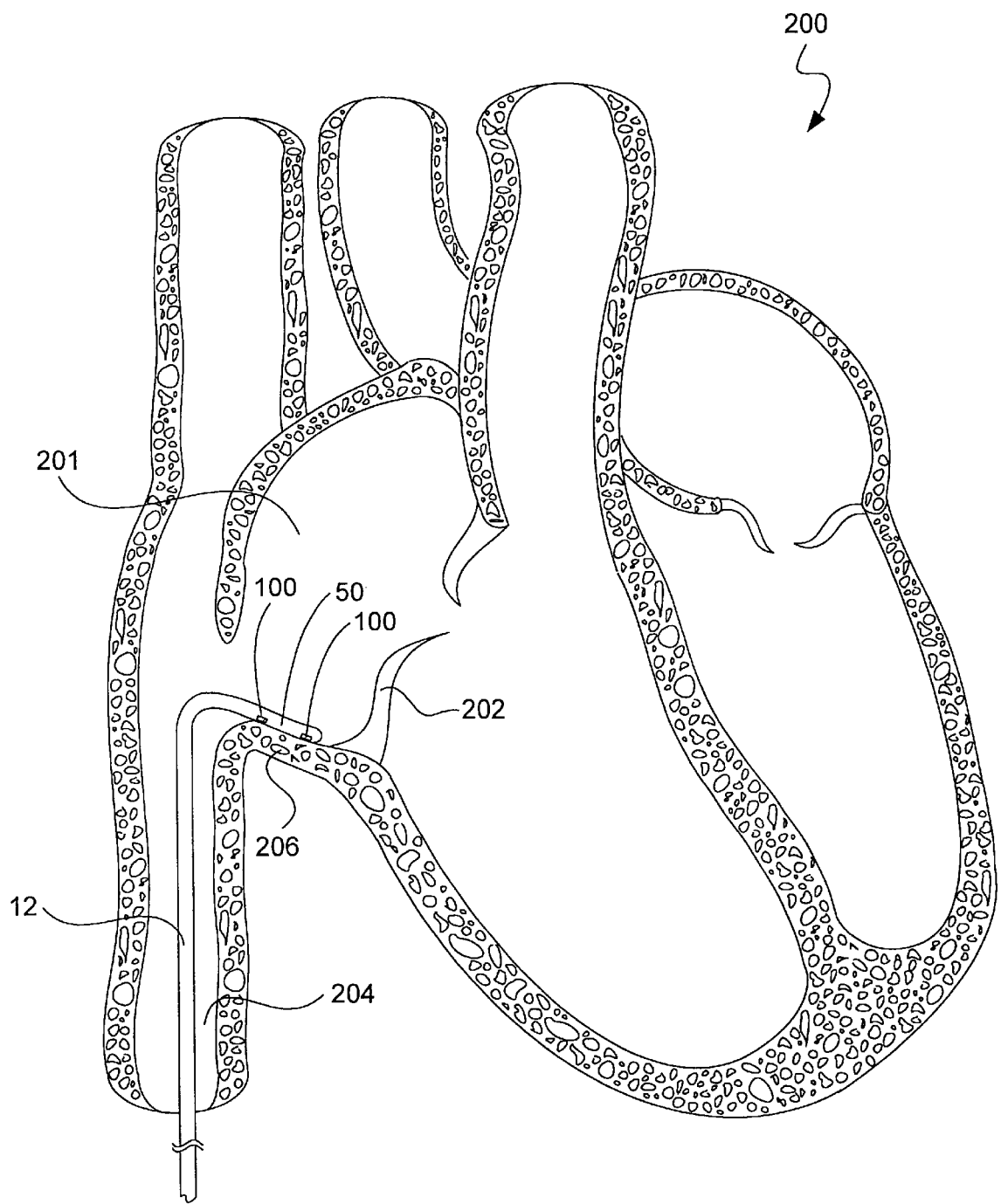
FIG. 9 is a cross-sectional view of a human heart showing the position of a catheter inside the right atrium, in accordance with one embodiment of the present invention.

One specific example for using the described catheter in a cardiac ablation procedure will now be described. In this example, the catheter may be fed through the femoral artery or other suitable vessel and into the appropriate region of the heart. Referring to FIG. 9, in order to treat type I atrial flutter, the antenna arrangement 50 is typically fed into the right atrium 201 of the heart 200 proximate the tricuspid valve 202 by steering the catheter 12 through the inferior vena cava 204. The electrode arrangements 100 will generally detect electrical signals in the adjacent regions of the heart, which will allow the physician to determine the appropriate ablation position. The catheter 12 may be withdrawn or further inserted as needed to position the antenna arrangement properly for the ablating procedure based on these electrical signals. In this example, once the physician receives a strong signal from the electrode arrangements 100, he/she will know that the directional component of the antenna arrangement 50 is in the appropriate direction for ablation.

After the antenna arrangement 50 is properly positioned at a target isthmus 206, electromagnetic energy is applied to the coaxial transmission line to facilitate ablation. Isthmus ablation is necessary to treat type I atrial flutter. During the ablation procedure, as well as after the operation is completed, the electrodes 100 may be used to monitor the ablation process as well as the results. When desirable, the catheter 12 can be further positioned after the ablation procedure to facilitate post procedure mapping or more ablation.

While the invention has been described in terms of a microwave ablation catheter for cardiac applications, it should be appreciated that the present invention could be used and in a wide variety of non-cardiac ablation applications as well. By way of example, the present invention may be used in most procedures relating to the ablation of biological tissues, in organs such as the heart (e.g., cardiac), the brain (e.g., cerebral), the prostate, the stomach, the liver, the intestines and the like.

Furthermore, although only a few embodiments of the present inventions have been described in detail, it should be understood that the present inventions may be embodied in many other specific forms without departing from the spirit or scope of the inventions. As such, the antenna and electrode arrangements have applications well beyond the field of microwave ablation catheters. By way of example, the antenna and electrode arrangements could also be used in a wide range of surgical devices. It is also contemplated that the catheter design may be widely modified without departing from the scope of this invention. By way of example, the electrode arrangement may be formed from a single electrode element or a plurality of electrode elements. Additionally, the described electrode arrangement could be used in a wide variety of ablation devices including RF catheters, cryoablation catheters, laser catheters or ultrasound catheters and various other surgical instruments.

Therefore, the present examples are to be considered as illustrative and not restrictive, and the invention is not to be limited to the details given herein, but may be modified within the scope of the appended claims.

What is claimed is:

1. A medical instrument, comprising:
    a transmission line suitable for the transmission of electromagnetic energy;
    an antenna coupled to the transmission line, and configured for generating an electromagnetic field sufficiently strong to cause tissue ablation, the antenna having a longitudinal axis; and
    a reflector arranged to be electrically coupled to the transmission line, the reflector being positioned laterally to a first side of the antenna and configured for redirecting a portion of the electromagnetic field to a second side of the antenna opposite the reflector,
    wherein a majority of the electromagnetic field is directed away from the second side of the antenna in a direction substantially perpendicular to the longitudinal axis of the antenna.

2. The medical instrument as recited in claim 1 wherein the reflector extends longitudinally and wherein the longitudinally extending reflector is positioned substantially in parallel with the longitudinal axis of the antenna.

3. The medical instrument as recited in claim 1 wherein the reflector and antenna extend longitudinally from the transmission line, and wherein the distal end of the reflector extends longitudinally to about the distal end of the antenna.

4. The medical instrument as recited in claim 1 wherein the reflector has an arcuate shape that flares towards the antenna.

5. The medical instrument as recited in claim 1 wherein the longitudinal axis of the antenna is offset from the longitudinal axis of the transmission line in a direction away from said reflector.

6. The medical instrument as recited in claim 1 wherein the instrument is one of a catheter or a surgical tool.

7. The medical instrument as recited in claim 1 wherein the instrument is suitable for ablating internal biological tissues including one of a heart, a brain, a prostate, a stomach, a liver or an intestine.

8. The medical instrument as recited in claim 1 wherein the frequency of the electromagnetic field is in the microwave range.

9. The medical instrument as recited in claim 1 wherein said medical instrument is suitable for ablating the isthmus between the tricuspid valve and the inferior vena cava to treat type I atrial flutter.

10. The medical instrument as recited in claim 1 wherein said medical instrument is suitable for creating linear lesions.

11. The medical instrument as recited in claim 10 wherein said linear lesions are suitable for use between any of the pulmonary veins to treat atrial fibrillation.

12. The medical instrument as recited in claim 10 wherein said linear lesions are suitable for use on the lateral wall of the right atrium from the superior to the inferior vena cava to treat one of type II atrial flutter and or atrial fibrillation.

13. A microwave ablation catheter, comprising:
a flexible tubular member having a lumen therein, and being adapted to be inserted into a vessel in the body of a patient;
a coaxial transmission line disposed within the lumen of the flexible tubular member, the coaxial transmission line including an inner conductor and an outer conductor suitable for the transmission of electromagnetic energy;
an antenna electrically coupled to the inner conductor of the coaxial transmission line, the antenna being positioned distally relative to the inner conductor and configured for generating an electromagnetic field sufficiently strong to cause tissue ablation, the antenna having a longitudinal axis; and
an arcuate electrically conductive reflector positioned to a first side of the antenna, the reflector being electrically coupled to the outer conductor of the coaxial transmission line, the reflector further being configured for redirecting a portion of the electromagnetic field to a second side of the antenna opposite the reflector,
wherein a majority of the electromagnetic field is directed away from the second side of the antenna in a direction substantially perpendicular to the longitudinal axis of the antenna.

14. The microwave ablation catheter as recited in claim 13 wherein:
the reflector and antenna extend substantially in parallel longitudinally from the transmission line;
the longitudinal axis of the antenna is offset from the longitudinal axis of the transmission line in a direction away from said reflector; and
the distal end of the reflector extends longitudinally to about the distal end of the antenna.

15. The microwave ablation catheter as recited in claim 13 wherein the distal end of the reflector extends longitudinally to at least the distal end of the antenna.

16. The microwave ablation catheter as recited in claim 13 wherein the reflector has an arc angle between about 90 and about 180 degrees.

17. The microwave ablation catheter as recited in claim 13 wherein the reflector is formed from stainless steel.

18. The microwave ablation catheter as recited in claim 13 wherein the ablation catheter further includes an antenna enclosure for encapsulating the antenna and the reflector, and being adapted to be inserted into a vessel in the body of a patient.

19. The microwave ablation catheter as recited in claim 13 wherein the ablation catheter further includes an impedance matching device for matching the impedance between the antenna and the coaxial transmission line.

20. The microwave ablation catheter as recited in claim 19 wherein the impedance matching device is disposed between the antenna and the inner conductor.

21. The microwave ablation catheter as recited in claim 19 wherein the impedance matching device is one of a capacitor, resistor, inductor, stub tuner or stub transmission line.

22. The microwave ablation catheter as recited in claim 13 wherein said medical instrument is suitable for ablating the isthmus between the tricuspid valve and the inferior vena cava to treat type I atrial flutter.

23. The microwave ablation catheter as recited in claim 13 wherein said medical instrument is suitable for creating linear lesions.

24. The microwave ablation catheter as recited in claim 23 wherein said linear lesions are suitable for use between any of the pulmonary veins to treat atrial fibrillation.

25. The microwave ablation catheter as recited in claim 24 wherein said linear lesions are suitable for use on the lateral wall of the right atrium from the superior to the inferior vena cava to treat one of type II atrial flutter and or atrial fibrillation.

26. An antenna arrangement for use in an ablation device, comprising:
a transmission line suitable for the transmission of electromagnetic energy;
an antenna coupled to the transmission line, and configured for generating an electromagnetic field; and
a reflector having an arcuate shape that flares towards the antenna, the reflector being positioned laterally to a first side of the antenna and configured for redirecting a portion of the electromagnetic field to a second side of the antenna opposite the reflector, wherein a majority of the electromagnetic field is directed away from the second side of the antenna, the electromagnetic field being sufficiently strong to cause tissue ablation proximate the second side of the antenna; and
an antenna enclosure for encapsulating the antenna and the reflector, and being adapted to be inserted into a vessel in the body of a patient.

27. The antenna arrangement as recited in claim 26 wherein the reflector is electrically connected to the transmission line.

28. The antenna arrangement as recited in claim 26 wherein the longitudinal axis of the antenna is offset from the longitudinal axis of the transmission line in a direction away from the reflector.

29. The antenna arrangement as recited in claim 26 wherein the ablation catheter further includes an impedance matching device for matching the impedance between the antenna and the coaxial transmission line.

30. The antenna arrangement as recited in claim 29 wherein the impedance matching device is disposed between the antenna and the inner conductor.

31. The antenna arrangement as recited in claim 29 wherein the impedance matching device is one of a capacitor, resistor, inductor, stub tuner or stub transmission line.

32. The antenna arrangement as recited in claim 26 wherein said medical instrument is suitable for ablating the isthmus between the tricuspid valve and the inferior vena cava to treat type I atrial flutter.

33. The antenna arrangement as recited in claim 26 wherein said medical instrument is suitable for creating linear lesions.

34. The antenna arrangement as recited in claim 33 wherein said linear lesions are suitable for use between any of the pulmonary veins to treat atrial fibrillation.

35. The antenna arrangement as recited in claim 33 wherein said linear lesions are suitable for use on the lateral wall of the right atrium from the superior to the inferior vena cava to treat one of type II atrial flutter and or atrial fibrillation.

36. A medical instrument, comprising:
- a transmission line suitable for the transmission of electromagnetic energy;
- an antenna coupled to the transmission line, the antenna extending substantially longitudinally from the transmission line, the antenna being configured for generating an electromagnetic field sufficiently strong to cause tissue ablation; and
- a reflector arranged to be electrically coupled to the transmission line, the reflector extending substantially longitudinally from the transmission line and in a direction substantially parallel to the antenna, the reflector cooperating with the antenna to direct the electromagnetic field in a direction opposite an inner peripheral surface of the reflector.

37. The medical instrument as recited in claim 36 wherein the reflector cooperates with the antenna to direct the electromagnetic field in a radial direction that is substantially perpendicular to the longitudinal axis of the medical device.

38. The medical device as recited in claim 1 wherein the reflector is a rigid structure.

39. The medical device as recited in claim 1 wherein the antenna and reflector are arranged to extend side by side in a substantially longitudinal direction.

40. The medical device as recited in claim 1 wherein the reflector has a concave cross sectional dimension taken transverse to the longitudinal axis of the reflector.

41. The medical device as recited in claim 40 wherein the concave cross section dimension extends partially around the periphery of the antenna.

42. The antenna arrangement as recited in claim 26 wherein the electromagnetic field is directed in a direction substantially perpendicular to a longitudinal axis of the antenna.

* * * * *